United States Patent [19]

Barabe

[11] Patent Number: 4,696,301
[45] Date of Patent: Sep. 29, 1987

[54] WOUND CLOSING METHOD

[76] Inventor: David J. Barabe, 2741 Lansdale La., Winston-Salem, N.C. 27103

[21] Appl. No.: 886,637

[22] Filed: Jul. 16, 1986

[51] Int. Cl.$^4$ ............................................. A61L 17/00
[52] U.S. Cl. .................................................. 128/335.5
[58] Field of Search .......................... 128/335.5, 334 R

[56] References Cited

U.S. PATENT DOCUMENTS

| | | |
|---|---|---|
| 2,387,131 | 10/1945 | Fernandez ........................... 128/335 |
| 2,409,261 | 10/1946 | Dow . |
| 3,520,306 | 7/1970 | Gardner et al. . |
| 3,698,395 | 10/1972 | Hasson . |
| 3,973,563 | 8/1976 | Green et al. ........................ 128/156 |
| 4,038,989 | 8/1977 | Romero-Sierra et al. . |
| 4,141,363 | 2/1979 | James et al. . |
| 4,222,383 | 9/1980 | Schossow . |
| 4,423,731 | 1/1984 | Roomi . |

OTHER PUBLICATIONS

"A Technique for Nonsuture Repair of Veins" by Healey, et al., Nov., 1961, pp. 267–271.

*Primary Examiner*—Richard C. Pinkham
*Assistant Examiner*—Gary Jackson
*Attorney, Agent, or Firm*—Richard E. Jenkins

[57] ABSTRACT

An incision-type wound closing suturing method including the steps of adhering a plurality of sutures to the patient's skin in spaced-apart relationship along each side of a wound and then tying together corresponding pairs of suture strands in order to close the wound to facilitate healing thereof. In one embodiment, the strands are adhered to the skin by first applying a small amount of glue at spaced intervals along each side of the wound and then placing an end of each suture strand in a respective one of the glue applications. In another embodiment, suture strands having an enlarged planar end are provided which may be utilized with the new suturing method.

2 Claims, 8 Drawing Figures

WOUND CLOSING METHOD

DESCRIPTION

1. Technical Field

The present invention relates to an improved suture and method of suturing for use in closing the edges of an incision-type wound in a patient's skin without piercing the skin tissue with a stitching needle and suture according to present surgical practice.

2. Background Art

Although various devices are known in the art which address the problem of closing a surgical wound without the necessity for piercing the skin tissue such as disclosed in U.S. Pat. No. 4,423,731 to Roomi, U.S. Pat. No. 2,409,261 to Dow and U.S. Pat. No. 2,387,131 to Fernandez, the most common method of closing an incision wound still utilizes the long standing practice of stitching with a needle and suture. This suturing process is painful and normally leaves scars at the piercing sites. Thus, a search continues for a better suturing method which will obviate the pain and scars associated with traditional stitching while still maintaining the effectiveness thereof.

DISCLOSURE OF THE INVENTION

In accordance with the present invention, applicant provides an improved suturing method and suture designed specifically to eliminate the pain and scars associated with traditional needle and suture closing of incision wounds. It is believed that this will be particularly helpful for physicians who must place sutures in children.

The invention provides a method and product for closing elongate-type incision wounds comprising adhering one end of a plurality of suture threads to the skin tissue along the length of each side of the incision wound and then tying together respective pairs of laterally spaced-apart suture threads into a plurality of suture knots in order to close the wound and maintain it in a closed position while healing takes place. The invention contemplates that the individual suture threads may be adhered to the patient's skin tissue with a small amount of glue applied from an appropriate container of fast drying and long lasting glue such as DURO superglue manufactured by Loc Tite Corporation of Cleveland, Ohio. Alternatively, each suture length may be provided with an adhesive element at the end thereof which is merely affixed to the patient's skin tissue at suitable locations along the length of the wound. Through the use of the suture method of the instant invention, a return visit to a physician for removal of the sutures is unnecessary since the sutures will naturally slough off after the healing process has occurred and the adhesive composition deteriorated.

It is therefore a primary object of the invention to provide an improved surgical suturing method for use as an alternative to conventional skin piercing suturing techniques.

A further object of the invention is to provide a simplified and painless suturing method with particular application to children having wounds requiring suture closing.

Some of the objects of the invention having been stated other objects will become evident as the description proceeds, when taken in connection with the accompanying drawings.

BEST MODE FOR CARRYING OUT THE INVENTION

Figure 1:
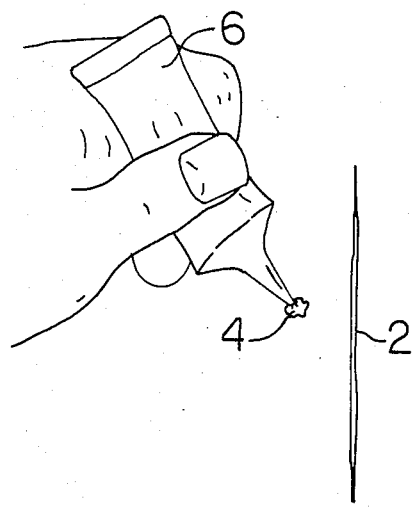
FIG. 1 illustrates in plan view a first stage in the incision-type wound closure.
Figure 2:
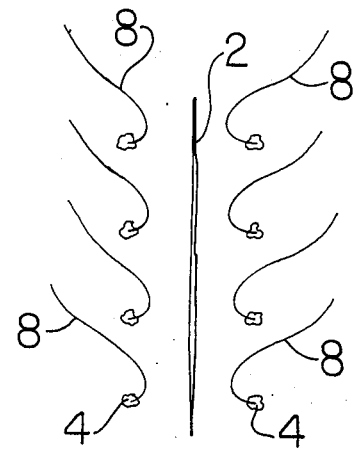
FIG. 2 illustrates in plan view an intermediate stage in the incision-type wound closure.
Figure 3:
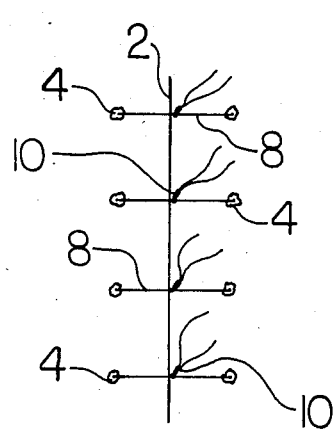
FIG. 3 illustrates in plan view the final stage in the incision-type wound closure method of the invention.
Figure 4:
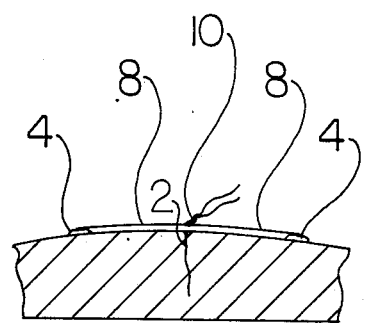
FIG. 4 illustrates a vertical cross-sectional view of a suture according to the present invention.

Referring to the drawings, FIG. 1 shows an elongate incision-type wound which requires surgical closure in order to properly heal. Rather than utilizing traditional needle and suture surgical closure which results in both pain and scarring due to the piercing of the skin tissue, the improved surgical method of the invention is utilized which includes first selectively applying glue spots 4 from a suitable glue source 6 along both sides of wound 2. It should be appreciated that glue 4 may most suitably be one of the new superglue compositions such as DURO superglue manufactured by Loc Tite Corporation. FIG. 2 shows a plurality of suture threads 8 of a determinate length which have each been secured to a respective glue spot 4 on an area of skin beside but laterally spaced from wound 2. Preferably, sutures 8 are secured to the skin adjacent wound 2 with glue spots 4 in laterally spaced-apart pairs which stradle wound 2. It should be fully appreciated that the suturing method up to this point could be accomplished by a nurse in order to free the physician for other necessary activity. Next, as best seen in FIGS. 3 and 4, the physician would close wound 2 by tying off laterally spaced-apart pairs of sutures 8 with knots 10. Knots 10 serve to close wound 2 and allow it to heal in a natural fashion. It has been found that glue 4 will secure sutures 8 to the skin of the patient for a period of at least 5 to 10 days before sloughing off and therefore provides sufficient time for wound 2 to heal. Moreover, painful removal of sutures by the physician is obviated by the new suturing method.

Figure 5:
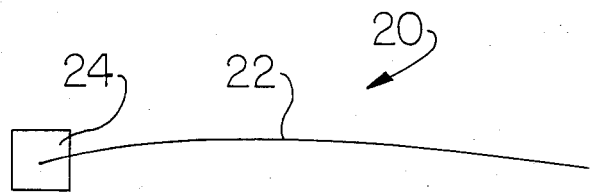
FIG. 5 illustrates a top plan view of a modified suture which may be used according to the invention.
Figure 6:
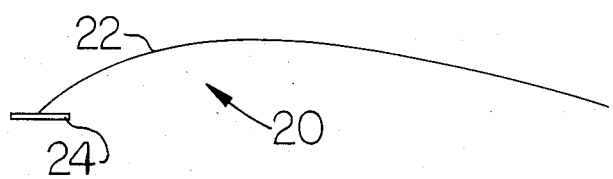
FIG. 6 illustrates a side elevation view of the suture shown in FIG. 5.

FIGS. 5 and 6 illustrate an improved suture 20 for use according to the invention which comprises a suture thread 22 secured to base member 24 which is most suitably of a generally flat or planar shape. Base member 24 may be constructed of a pliable vinyl, plastic or textile material. Base member 24 may be applied to glue spots 4 according to the method of the invention and serves to affix the sutures to the skin of the patient.

Figure 7:
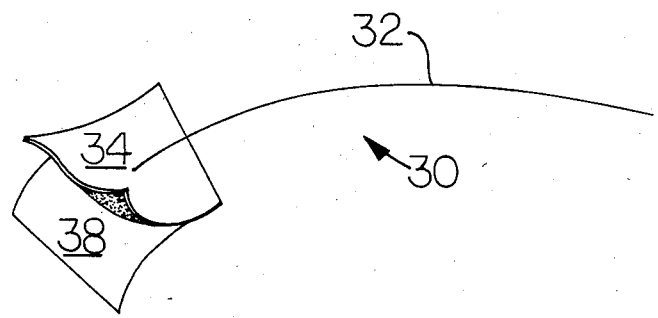
FIG. 7 illustrates in perspective view another suture which may be used according to the present invention.
Figure 8:
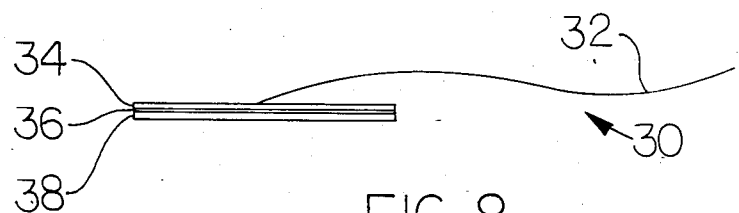
FIG. 8 illustrates a side elevation view of the suture of FIG. 7.

Another novel suture contemplated for use to practice the surgical suturing method of the invention is shown in FIGS. 7 and 8 and generally designated 30. While similar to the suture shown in FIGS. 5 and 6, this suture comprises not only suture thread 32 and base member 34 but also provides for an adhesive layer 36 on the bottom of base member 34 and protected by cover 38 which may be peeled away therefrom and discarded when the nurse or physician is ready to secure suture 30 to a patient's skin. With the use of suture 30 it is not necessary to utilize glue spots 4 which have been described hereinbefore. Glue 36 on the patient contact side of base member 34 of suture 30 is also of a similar long-adhering composition such as has been described above.

It will be understood that various details of the invention may be changed without departing from the scope thereof. Furthermore, the foregoing description is for the purpose of illustration only and not for the purpose of limitation—the invention being defined by the claims.

What is claimed is:

1. A surgical method for closing an elongate wound of a patient without requiring piercing of the skin comprising:

applying a small amount of glue to the patient's skin at spaced intervals along each side of the wound and then placing one end of each of a plurality of suture threads into a respective one of said spaced glue applications until it is adhesively secured to the skin;

tying together laterally spaced-apart suture threads into a plurality of suture knots in order to close the wound and maintain it in a closed condition to facilitate healing thereof; and maintaining the tied sutures in place until the wound heals.

2. A surgical method for closing an elongate wound of a patient without requiring piercing of the skin comprising:

applying a small amount of glue to the patient's skin at spaced intervals along each side of the wound and then placing one end of each of a plurality of suture threads, said end comprising an enlarged substantially planar base member, into a respective one of said spaced glue applications until it is adhesively secured to the skin;

tying together laterally spaced-apart suture threads into a plurality of suture knots in order to close the wound and maintain it in a closed condition to facilitate healing thereof; and maintaining the tied sutures in place until the wound heals.

* * * * *